United States Patent [19]

Ng et al.

[11] Patent Number: 4,495,087

[45] Date of Patent: Jan. 22, 1985

[54] PREPARATION OF ALUMINUM HYDROXYCARBONATE GELS BY A CONTINUOUS PROCESS

[76] Inventors: Tai-Wing Ng, Downsview; Arthur P. G. Wright, Toronto; Eric Blaser, Toronto; Suhas Ambike, West Hill, all of Canada

[21] Appl. No.: 452,997

[22] Filed: Dec. 27, 1982

[51] Int. Cl.³ .................. B01J 13/00; C01F 7/02; A61K 33/08
[52] U.S. Cl. .................. 252/315.7; 423/629; 423/630; 424/157
[58] Field of Search ............ 252/317, 315.7; 423/635, 628, 629, 630; 424/157

[56] References Cited

U.S. PATENT DOCUMENTS

| | | | |
|---|---|---|---|
| 3,617,585 | 11/1971 | Haas et al. | 252/635 |
| 3,773,918 | 11/1973 | Beekman | 423/629 |
| 3,911,090 | 10/1975 | Hein et al. | 423/629 |
| 3,951,852 | 4/1976 | Gregory et al. | 252/317 |
| 4,053,568 | 10/1977 | Madaus et al. | 424/157 |
| 4,105,579 | 8/1978 | Glasscock | 252/315.7 |

Primary Examiner—Richard D. Lovering
Assistant Examiner—Anne Brookes
Attorney, Agent, or Firm—Daniel A. Scola, Jr.; Gary M. Nath

[57] ABSTRACT

Aluminum hydroxycarbonate gel is precipitated under highly homogeneous conditions by continuously introducing an aluminum salt solution and an alkaline-reacting carbonate and bicarbonate solution into a vigorously agitated reactor vessel and continuously withdrawing the reaction mixture.

27 Claims, 4 Drawing Figures

PREPARATION OF ALUMINUM HYDROXYCARBONATE GELS BY A CONTINUOUS PROCESS

This invention relates to a process for the production of aluminium hydroxycarbonate gel.

Aluminium hydroxide gel has been used as an effective antacid for decades, and has commonly been prepared by hydrolysis of aluminium salt solutions with an aqueous alkaline solution. It is known that, depending on the nature of the reactants, the gel product can contain various non-hydroxyl anions. In particular, it is known that by reacting an aqueous solution of an aluminium salt with an aqueous alkaline solution containing carbonate and bicarbonate anion, an aluminium hydroxide gel having especially good antacid properties can be obtained. This product has a polymeric aluminium hydroxide structure, with the carbonate anion being integrally incorporated into the polymeric structure, and is referred to as aluminium hydroxycarbonate gel.

As far as the inventors are aware, in processes that have previously been employed on a commercial scale for production of aluminium hydroxycarbonate gel, relatively dilute reactant solutions have been employed, and these solutions have been introduced at somewhat slow rates of addition to reaction vessels wherein the reaction mixture is thoroughly agitated, in order to reduce as far as possible loss of carbonate anion through evolution of carbon dioxide as a result of reaction with local concentrations of the usually acid-reacting aluminium salt solution. As a result, large capacity reaction vessels have had to be employed in order to hold the large volumes of reaction solutions, and the rates of production of the gel product have not been very high.

The present invention provides a process for the production of aluminium hydroxycarbonate gel comprising reacting an aqueous solution of an aluminium salt with an aqueous alkaline solution containing carbonate and bicarbonate anion and that undergoes reaction with the aluminium salt to precipitate therefrom an aluminium hydroxycarbonate gel, said process comprising continuously introducing the reactant solutions into an initial reactor vessel wherein the gel-forming reaction takes place, the reaction mixture being vigorously agitated so as to maintain the reactants and the gel precipitate formed therefrom substantially homogeneously distributed throughout the vessel, continuously withdrawing from the initial reactor vessel an output stream of the reaction mixture containing aluminium hydroxycarbonate gel, passing the reaction mixture to a subsequent reaction vessel, and permitting the gel-forming reaction to proceed in the said subsequent vessel.

With this process, as there is continuous introduction of reactants and continuous withdrawal of reaction mixture, this permits the use of a relatively small reactor vessel in which the average residence time of the reactants can be quite brief, and within this small volume of reaction mixture, efficient mixing of the reactants can be more readily achieved, so that the reaction mixture can be made highly homogeneous. It is considered that highly homogeneous precipitation conditions promote the formation of a gel product having good antacid properties. The present process moreover permits the use of relatively high concentrations of the reactant solutions, especially of the aluminium salt solution, without undue loss of carbonate anion, and greater yields of the gel product can be obtained.

In the preferred form, at least one of, and more preferably both of, the reactant solutions are injected under pressure into the reactor vessel from injection points located below the surface of the reaction mixture. The reactants can be injected through fine-sized, divergently-arranged nozzles or in some other manner that causes the injected reactant solution to be rapidly dispersed within the reaction mixture. Injection of the reactants allow for very rapid mixing of the reactant liquids to yield a homogeneous reaction mixture.

Normally, it is desired to conduct the precipitation reaction at a particular pH selected to so control the hydrolysis reaction as to yield gel precipitate particles of large size, and to promote the incorporation of the carbonate anion into the polymeric structure. As the rates of inflow of reactants into the reactor vessel will usually be high, it can be difficult to avoid variations in the pH of the reaction mixture as a result of small variations in the rates of inflow or in the concentrations of the respective reactant solutions and, as noted above, there is a risk that local concentrations of acid-reacting aluminium salt solution may cause loss of carbonate anion through evolution of carbon dioxide. Moreover, owing to the short residence time in the reactor vessel, many of the gel particles in the reaction mixture will not have grown to a particle size that permits them to be readily filtered off from the reaction mixture.

It is therefore preferred to maintain the reaction mixture in the initial reactor vessel at a relatively higher (more alkaline) pH and to feed the output stream from the initial reactor vessel continuously to a subsequent reaction vessel of relatively larger capacity wherein the reaction mixture resides for a period permitting growth of the particles of precipitated gel, whereby separation of the particles of gel from the liquid phase is facilitated, the mixture being maintained in said ageing vessel at substantially constant relatively lower (more acidic) pH through controlled additions of an aqueous acidic solution of an aluminium salt and being vigorously agitated so as to maintain the reaction mixture in a substantially homogeneous condition, a continuous stream of reaction mixture containing gel particles of increased size being withdrawn from said subsequent reaction vessel.

Since, even after residence in a subsequent reaction or ageing vessel, the reaction mixture may contain numerous gel particles or micelles that cannot readily be separated from the reaction mixture using the usual kinds of the solid-liquid separator devices, it is advantageous to conduct the process in such manner that, after the gel-forming reaction is substantially complete, the gel is permitted to separate from the reaction mixture to form a gel precipitate phase and a supernatant phase containing small suspended particles of aluminium hydroxycarbonate gel, and the supernatant phase is withdrawn and recycled to the reactor vessel. Similarly, the filtrate recovered in subsequent gel-filtering steps, and any aqueous washings recovered in subsequent procedures for washing the gel product to reduce its content of water-soluble impurities, may also be recycled to the reactor vessel. In this manner, the efficiency of the reaction is improved as small size gel particles are thereby cycled round the system until they attain sufficient particle size to be separated off and recovered with the main body of the gel product, and, moreover, unreacted aluminium salt and/or carbonate and bicarbonate solutions can be returned to the reaction system.

BRIEF DESCRIPTION OF DRAWINGS

The present invention will now be more fully described, by way of example only, with reference to the accompanying drawings, wherein.

Figures 1, 2:
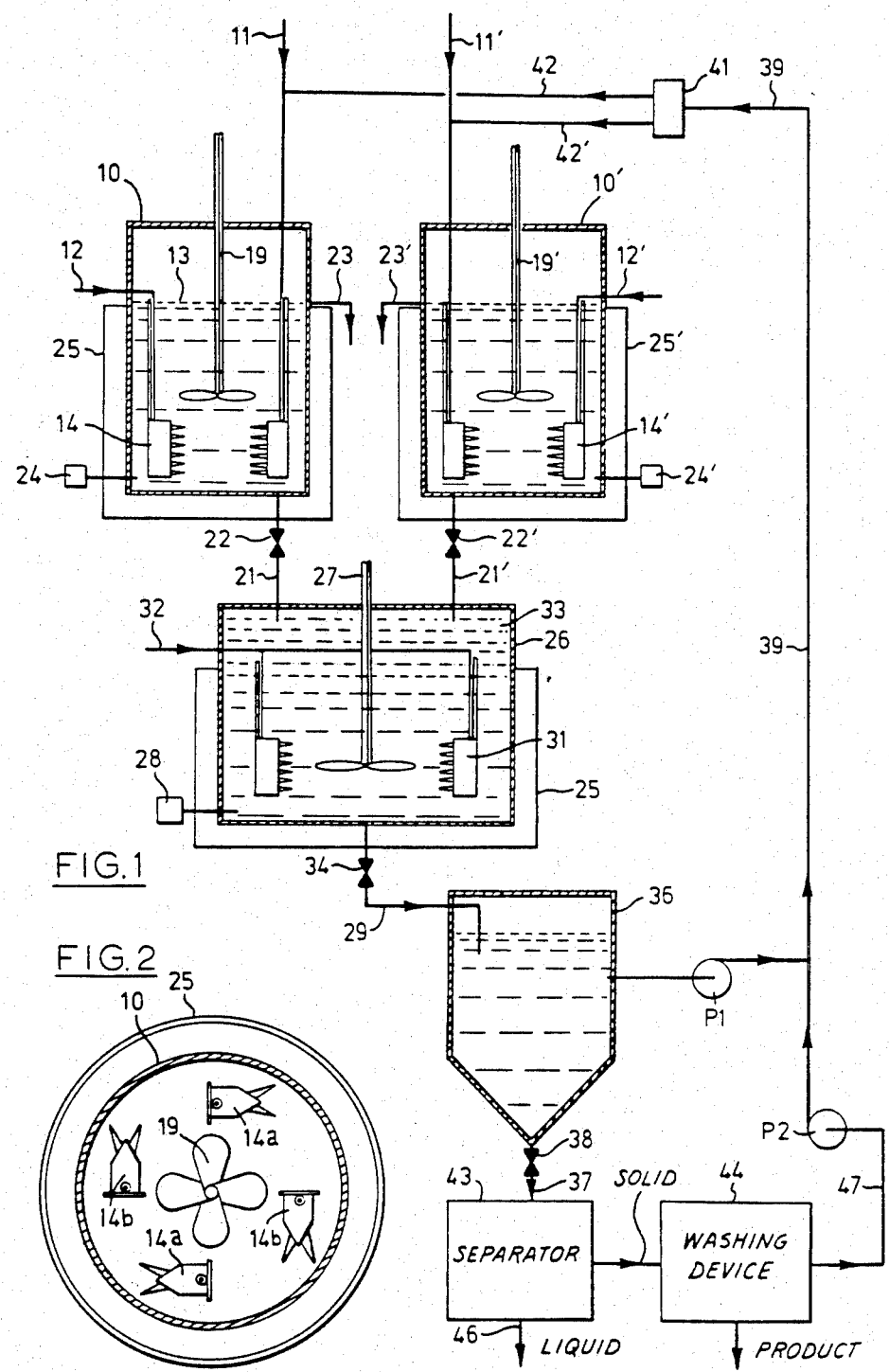
FIG. 1 shows partly schematically, and partly in vertical section, one form of apparatus for use in carrying out the method of the invention.
FIG. 2 shows a horizontal cross-section through a reactor vessel employed in the apparatus of FIG. 1, taken on the line II—II.
Figure 3:
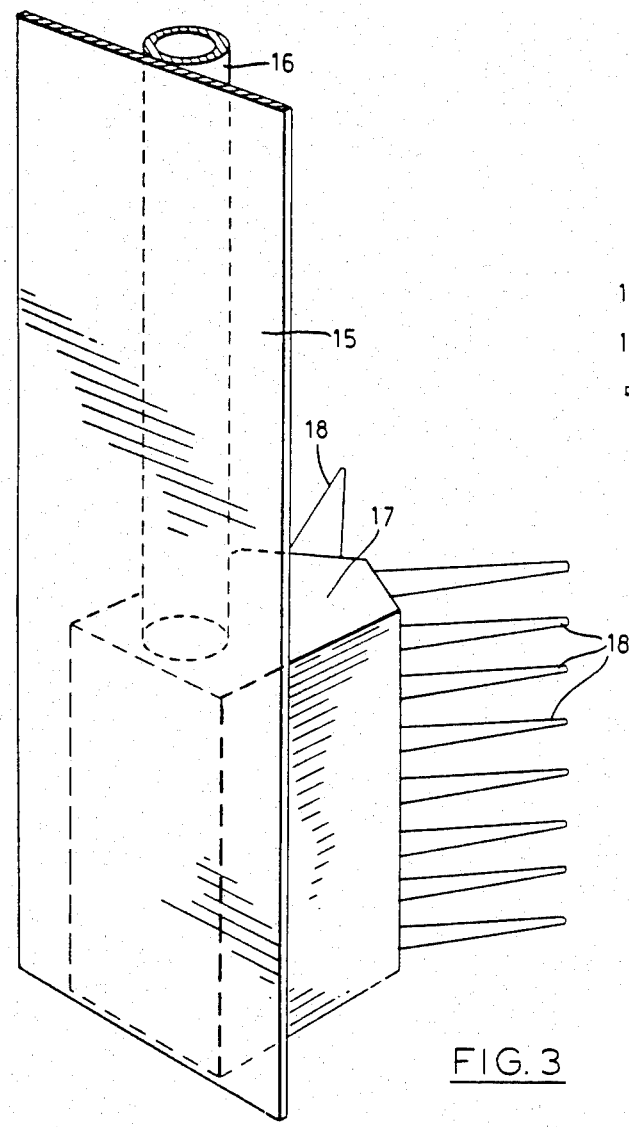
FIG. 3 shows a perspective view of an injection unit employed in the reactor vessels of FIG. 1.
Figure 4:
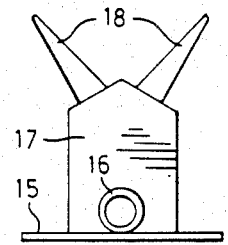
FIG. 4 shows a plan view of the injection unit of FIG. 3.

Referring to the drawings, wherein like reference numerals indicate like parts, in FIG. 1, a reactor vessel 10 has inlets 11 and 12 for introduction of a mixed carbonate and bicarbonate solution, and an aluminium salt solution, respectively. Each solution enters the reaction mixture 13 contained within the reaction vessel through an injection unit 14, as illustrated in more detail in FIGS. 3 and 4. Each unit comprises a delivery tube 16 connecting at its lower end with a header box 17 on which are disposed two divergent rows of nozzle pieces 18. Preferably each nozzle piece 18 comprises a tube of plastic or other inert material that tapers toward a capilliary-sized orifice at the tip. In the preferred form, as illusrated in FIG. 2, there are two or more injection units for each reactant solution, with pairs of the injection units 14a for the aluminium chloride solution and 14b for the carbonate and bicarbonate solution being arranged diametrically opposite one another within the reactor vessel 10 and having their injection nozzles 18 positioned generally tangentially, so that a swirling motion is imparted to the reaction mixture 13. The reactor vessel 14 is provided with a conventional form of agitator 19 which is operated at medium rotational speeds in the sense conforming to the rotation of the vortex created by the injection units 14. At the bottom of the reactor vessel there is an outlet 21, and the rate of outflow of the reaction mixture is controllable by means of a valve 22. At the upper end of the reactor vessel 10 is an overflow 23, and the inflow of reactants through the lines 11 and 12 is maintained slightly in excess of that leaving through the output line 21, so that a small outflow is maintained through the overflow 23, thereby maintaining an approximately constant level of reaction mixture within the reactor vessel 10.

As can be seen from FIG. 2 in the preferred arrangement the injection units 14 include radially orientated baffle plates 15 which are arranged radially so as to create turbulence within the reactor vessel, thus promoting homogeneous mixing of the contents of the reaction mixture.

On start-up of the process, the reactor vessel 10 may first be filled with a mixture of carbonate and bicarbonate solutions in the desired proportions, and then, with the agitator 19 being operated under high mass transfer conditions, injection of the aluminium salt solution through the input line 12 and injection units 14a is commenced simultaneously with injection of a mixed carbonate and bicarbonate solution through the input lines 11 and injection units 14b, and outflow of reaction mixture at a corresponding flow rate is commenced through the output pipe 21. The injection of the solution through the injector units 14a and 14b is made with the solutions under positive pressure so that penetration of the reaction mixture 13 back into the capilliary nozzle 18 is prevented.

In the preferred form, the aqueous aluminium solution consists of a solution of aluminium chloride. Although aluminium chloride is normally preferred, other aluminium salt solutions that will react with alkaline carbonate and bicarbonate, for example aluminium sulphate solution, can of course be employed. One advantage of the process as illustrated in the drawings is that relatively high concentrations of aluminium salt solution can be employed, as, owing to the highly efficient mixing conditions that can be achieved in the continuous reactor 10, local concentrations of concentrated acid-reacting aluinium salt solution can be substantially avoided, whereby loss of carbonate anion through evolution of carbon dioxide is much reduced. For example, in the case of aluminium chloride solution, solutions of up to about 33% by weight concentration may be employable. All concentrations by weight of aluminium chloride solutions herein refer to the weight of aluminium chloride hexahydrate dissolved in the solution. However, owing to the restricted commercial availability of concentrated aluminium salt solutions, it may be more convenient to employ solutions of somewhat lesser concentration. Preferably, the concentration of the solution is at least 10% by weight, based on the total weight of the solution, and in the preferred form an aluminium chloride solution of 20 to 30% by weight concentration (based on the weight of aluminium chloride hexahydrate) is employed. More generally, the aluminium salt solution may contain from about 0.4 to about 1.6 moles $Al^{3+}$ ion per liter, more preferably from about 0.9 to about 1.4 moles $Al^{3+}$ ion per liter.

In the preferred process, the alkaline carbonate and bicarbonate solution comprises a solution of alkaline metal carbonate and bicarbonate although other water-soluble alkaline-reacting carbonate and bicarbonate solutions may be employed e.g. ammonium carbonate and ammonium bicarbonate. Because of their low cost and widespread availability, the use of sodium carbonate and sodium bicarbonate is preferred, although in the case of the production of specialized sodium-free gel products, a mixture of potassium carbonate and potassium bicarbonate may be employed instead.

Preferably, the alkaline solution fed through the inlet line 11 contains from about 2 to 6% by weight sodium carbonate, more preferably about 2.8% by weight, while the bicarbonate content ranges from about 3.0 to about 8% by weight, more preferably about 4.5% by weight. In more general terms, this alkaline solution should preferably contain from about 0.1 to about 0.6 moles $CO_3^{2-}$ ion per liter from about 0.2 to about 1.0 moles $HCO_3^-$ ion per liter, more preferably from about 0.2 to about 0.3 moles $CO_3^{2-}$ ion per liter and from about 0.5 to about 0.6 moles $HCO_3^-$ ion per liter.

In order to conduct the mixing of the reactant liquids efficiently within the reactor vessel 10, the volume of the reaction mixture 13 within the vessel 10 should be kept substantially constant and, in the example illustrated, this is ensured by feeding reactant in through lines 11 and 12 at a rate slightly higher than the outflow through line 21 and taking a small overflow over the weir 23. Under the above described reaction conditions, the reaction mixture within the reactor vessel 10 should be maintained as far as possible in a completely homogeneous state, so that there are no local concentrations of aluminium salt solution that may cause loss of carbonate anion through evolution of carbon dioxide. Normally, it is desirable to maintain the contents of the reactor vessel at as far as possible a selected pH which has been determined to promote precipitation of the aluminium hydroxide gel to form good-sized gel particles, with satisfactory incorporation of carbonate anion into the hydroxide gel structure. In the case of reaction of aluminium chloride solution with sodium carbonate and bicarbonate, it is desirable to conduct the precipitation at about pH 6.5. The reactor vessel 10 may be provided adjacent its outlet 22 with a pH-measuring probe 24, whereby the pH of the reaction mixture exiting from the reactor vessel may be monitored, and the rates of flow of the alkaline and acidic reactant solutions entering through the lines 11 and 12 may be adjusted so as to control the pH within a required range.

Owing to the high flow rates of the reactant solutions that are fed into the reactor vessel 10, and because it is difficult to avoid small fluctuations in these flow rates or in the concentrations of the respective reactant solutions, it is difficult to control the pH of the reaction mixture within the reactor vessel 10 closely, and moreover, as the residence time of the reaction mixture in the reactor 10 is relatively brief, the reaction mixture exiting through the output line 21 contains substantial quantities of particles of gel of relatively small size that cannot be readily separated from the reaction mixture using solids-liquids separator devices of the conventional type. Normally, the reaction mixture exiting through the line 21 will also contain substantial quantities of unreacted carbonate and bicarbonate. In order to permit growth of the gel particles within the reaction mixture to a larger particle size that renders them more separable from the liquid phase, and also to permit continued reaction of unreacted materials under more closely controlled conditions of pH, it is preferred to adjust the ratio of the reactant liquids supplied to the reactor vessel 10 so that the pH of the reaction ixture exiting the reactor vessel 10 is slightly more alkaline than that required for optimum precipitation conditions, and to feed the mixture continuously to a subsequent reaction vessel comprising a precipitate ageing vessel 26, wherein the reaction mixture is maintained thoroughly agitated and in a substantially homogeneous condition by an agitator or stirrer 27, and the pH of the mixture is maintained at a relatively lower (more acidic) substantially constant value through controlled introduction of an aqueous acidic aluminium salt solution. Measurements of pH of the reaction mixture within the ageing vessel 26 is conducted using a pH measuring probe 28 adjacent the lower region of the vessel 26, from which an output is taken through an output line 29.

Controlled additions of acidic aluminium salt solution are made to the ageing tank in accordance with the pH measurements obtained with the probe, so that the pH of the mixture in the vessel 26 is maintained at a substantially constant value. The acidic solution preferably is injected into the vessel 26 through an arrangement of injection units 31 similar to the units 14 employed in the reactor vessel 10. These injection units 31 are supplied through a feed line 32, and provide for very rapid and efficient homogeneous dispersion of the aluminium salt solution throughout the body of reaction mixture 33 maintained within the vessel 26.

The aluminium salt solution introduced in the ageing vessel may be any aqueous acid-reacting aluminium salt that is compatible with the reactants and that will react with unreacted carbonate and bicarbonate in the reaction mixture received from the reactor vessel, but usually it is more convenient to employ a solution of an aluminium salt the same as that introduced in the reactor vessel 10. The solution is, however, normally considerably more dilute than the solution employed in the reactor vessel 10, so that additions of relatively small quantities of the acidicreacting substance can be made with precision. In the case where the acidic solution is an aqueous solution of aluminium chloride, this will preferably be a solution of about 5 to about 15% by weight concentration, (based on the weight of the hexahydrate) more preferably about 10% by weight concentration. More generally, the acidic solution preferably contains from about 0.2 to about 0.7 moles $Al^{3+}$ ion per liter, more preferably about 0.4 to about 0:5 moles $Al^{3+}$ ion per liter.

In the ageing vessel 26, it usually will be desired to maintain the reaction mixture at a substantially constant pH in the range of about 6.4 to about 6.8. In the case of the reaction between aluminium chloride solution and sodium carbonate and sodium bicarbonate solution, it is desirable to maintain the reaction mixture in the ageing tank at a substantially constant pH of about 6.5. The reaction mixture is maintained within the ageing tank 26 under substantially homogeneous conditions for an adequate residence time, sufficient to allow substantially complete reaction of the aluminium salt solution with the alkaline carbonate and bicarbonate solution, and to permit the gel particles to increase in size to a desired extent, permitting their more ready separation from the liquid phase of the reaction mixture at a subsequent stage. A continuous outflow of the reaction mixture is taken from the ageing vessel 26 through the outflow line 29 under the control of an adjustable valve 34.

In order to avoid impairing the antacid properties of the gel product, it is desirable to conduct the gel-forming reaction at below ambient temperatures, typically in the range of about 0° C. to 5° C. For this purpose, the reactant solutions are preferably pre-cooled before being introduced into the reactor vessel 10 and ageing vessel 26, and these vessels may be provided with thermally-insulative jackets 25 to reduce absorption of heat from the surroundings.

In order to increase the throughput of materials while still retaining the capability to conduct a thorough and efficient mixing and homogenisation of the reactant solutions in a relatively small reactor vessel, it may be desired to employ two or more reactor vessels feeding into the ageing vessel 26. In FIG. 1, a second reactor vessel 10' is employed, feeding into the ageing vessel through an outlet line 21'. The construction and operation of the second reactor vessel 10' is in all respects similar to that described above for the reactor 10.

The ageing vessel 26 may be maintained substantially full of the reaction mixture 33 at all times, as illustrated in FIG. 1, or the vessel 26 may be provided with a weir overflow similar to the overflow 23 or 23' employed for the vessel 10 or 10', and the feed of reactant liquids to the vessel through the lines 21, 21' and 32 may be arranged to be slightly greater than the output flow through the line 29, to ensure that a constant volume of liquid is maintained in the vessel 26.

Before subjecting the reaction mixture exiting from the ageing vessel 26 to a solids-liquids separation step to remove excess liquids, it is desirable to concentrate the solids content, and this can be performed by feeding the output from the ageing vessel 26 into a conventional form of thickener vessel 36 in which the slurry of the gel precipitate is allowed to settle slowly to the bottom and subsequently exit continuously through an underflow outlet pipe 37, under the control of a flow-controlling valve 38 to the separator unit. The overflow or supernatant liquid from the upper part of the thickener vessel 36 is withdrawn through a pump P1. This supernatant liquid contains small sized gel particles or micelles, and after adjusting the concentration with fresh raw materials, the supernatant liquid is recycled to the reactor vessel 10 along a line 39. Where two or more reactor vessels are employed, the flow of recycled liquid may be divided at a flow dividing valve 41, and in the example shown in FIG. 1, half the flow is returned to the reactor vessel 10 along line 42 and the other half is returned to reactor vessel 10' along the line 42'. The undersized gel particles thereby recycled to the reactor vessel 10 or 10' can coagulate to form larger gel particles which can be removed from the main body of the gel product during a subsequent settling step in the thickener vessels 36.

When the process is operated in accordance with the preferred procedure as described above, the gel slurry withdrawn from the ageing tank along the line 29 normally contains excess unreacted carbonate anion, and this will also be recycled to the reactors 10 or 10' with the recycled stream along the line 42 and 42' for further reaction.

The thickened gel precipitate slurry withdrawn from the thickener vessel 36 through line 37 is passed to a solids-liquids separator unit 43. Preferably, a continuously-operating solids-liquids separator device is employed, and advantageously this is a continuous belt vacuum filter. In order to reduce the content of water-soluble impurities in the product, especially the content of sodium or potassium salts where sodium or potassium carbonate and bicarbonate are employed as the alkaline-reacting carbonate and bicarbonate solution, the gel product is washed with water in a washing device 44, to yield the final gel product. The liquids separated at the separator device 43 and the washings from the washing device 44 are preferably also recycled to the reactors 10 and 10'. In the example shown in FIG. 1, therefore, the liquid withdrawn from the separator device along a line 46 is passed to a line 47 and the liquid is pumped through pump P2 to the main recycle line 39. Conveniently, the functions of solids-liquids separation and washing can be combined in a single unit, for example a continuous belt vacuum filter equipped with a water spray washer that washes the filtered solids residue. In this manner, any unreacted carbonate in the separated liquid and in the washings obtained from the washing device can be recycled to the reactors 10 and 10', together with any small-sized gel particles that pass over into the liquid phase at the solids-liquids separator. Where overflow weirs are used to control the levels in the reactor vessels 10 or 10' or in the ageing vessel 26, the small quantities of overflow liquids may be recycled to the reactors 10 or 10' along the recycling line 39.

Preferably, where an alkali metal carbonate and bicarbonate solution are employed as the alkaline-reacting carbonate and bicarbonate reactants, the washing step is so conducted as to yield in the solids residue a content of no more than about 0.5% by weight of the alkali metal cation based on the weight of the wet gel product, preferably no more than about 0.1% by weight.

Although the above disclosure taken in conjunction with the accompanying drawings provides ample information to one skilled in the art to permit the production of an aluminium hydroxy-carbonate gel, for the avoidance of doubt a detailed example of one form of gel-forming process in accordance with the invention will now be given.

EXAMPLE

Employing the apparatus as illustrated in FIG. 1, the reactor vessel 10 having a capacity of approximately 75 liters was first charged with 10 liters of mixed carbonate and bicarbonate solution (4.5% sodium bicarbonate and 2.8% sodium carbonate anhydrous). This is enough to well cover the blades of the stirrer 19. Introduction of Al $Cl_3.6H_2O$ (30%) solution and of the said mixed carbonate and bicarbonate solution was then commenced through the inlet lines 12 and 11, feeding these solutions through the injection units 14a and 14b, respectively. Over the total period of the run, which lasted for about 4½ hours, about 40 liters of the aluminium chloride solution and about 800 liters of the mixed carbonate and bicarbonate solution were added, the rates of addition of the two solutions being adjusted so that the pH of the reaction mixture 13 in the reactor vessel 10 remained between 6.6 and 7.0. The two solutions were pre-cooled to 2° to 3° C. before being introduced into the reactor vessel 10, so that the temperature of the solutions in the reactor vessel 10 and in the ageing vessel 26 was kept below 5° C.

Once the volume of the reaction mixture in the reactor vessel 10 exceeded approximately 50 liters, continuous discharge of the reaction mixture into the ageing vessel 26 (of capacity 125 liters) was commenced, where the pH was maintained at 6.5 by continual additions of 10% Al $Cl_3.6H_2O$ solution, about 15 liters being added, through the injectors 31, over the whole period of the run.

With the ageing vessel 26 full of liquid, discharge of liquid was commenced into the thickener 36 where the solids content of the underflowing slurry was concentrated to over 30% by weight. The underflow was filtered by a vacuum drum filter and the wet cake was then thoroughly washed to remove the undesirables (chiefly sodium chloride), using approximately 35 volumes of water per volume of gel. The mother liquor in the thickener 36 and some filtrate were transferred to a storage tank (500 liters) the concentration of which was adjusted with saturated solutions of sodium carbonate and sodium bicarbonate. This mixture of carbonates was used for further reaction. The total yield of the washed aluminium hydroxycarbonate gel was 29.5 kg (11.6% $Al_2O_3$ content).

The properties of the aluminium hydroxycarbonate gel obtained following the procedure of the detailed Example were investigated. The acid consuming capacity was conducted in accordance with the procedure in U.S. Pharmacopeia, 19th rev. 1975, page 21. The acid neutralization properties of the gel product were determined by conducting the pH-stat titration described by Kerkhof et al, J. Pharm. Sci., Vol. 66, 1528 (1977). This pH stat titration determines the acid neutralization rate at a constant pH (pH 3.0) during the whole course of the reaction, and simulates the in vivo gastric acid neutralization reaction. The results were as shown in the following Table.

TABLE

| | % $Al_2O_3$ (w/w) | % Na (w/w) | ACP* (USP) | $T^{100}$ (min) | $T^{90}$ (min) | $T^{50}$** (min) |
|---|---|---|---|---|---|---|
| Gel product of Example | 11.6 | 0.5 | 23→25 | 10 | 4 | 3 |

*ACP, acid consuming capacity, is the number of milliliters of 0.1N Hydrochloric acid required to neutralize one gram of gel containing 4% $Al_2O_3$ at pH 3.5.
**$T^{50}$, $T^{90}$, $T^{100}$ are the times in min. required to add 50, 90, 100% respectively of the total 1.0N HCl needed to neutralize the aluminum hydroxide gel present maintaining the pH of the mixture at 3.0 throughout.

The embodiments of the invention in which an exclusive property or privilege is claimed are defined as follows:

1. Process for the production of aluminum hydroxycarbonate gel comprising reacting an aqueous solution of an aluminum salt with an aqueous alkaline solution containing carbonate and bicarbonate anion and that undergoes reaction with the aluminum salt to precipitate therefrom an aluminum hydroxycarbonate gel, said process comprising continuously introducing the reactant solutions into an initial reactor vessel wherein the gel-forming reaction takes place, the reaction mixture being vigorously agitated so as to maintain the reactants and the gel precipitate formed therefrom substantially homogeneously distributed through the vessel and wherein the reaction mixture in the initial reactor vessel is maintained at a pH from about 6.5 to about 7.0, by controlled addition of an aqueous solution of an aluminum salt, continuously withdrawing from the initial reactor vessel an output stream of the reaction mixture containing aluminum hydroxycarbonate gel, passing the reaction mixture to a subsequent reaction vessel wherein the reaction mixture is maintained at a lower pH of about 6.4 to about 6.8, and permitting the gel-forming reaction to proceed in the said subsequent vessel.

2. Process as claimed in claim 1 wherein at least one of the reactant solutions is injected under pressure into the initial reactor vessel from an injection point below the surface of the reaction mixture in such manner that the injected reactant solution is dispersed within the reaction mixture.

3. Process as claimed in claim 2 wherein both reactant solutions are injected into the reaction mixture.

4. Process as claimed in claim 2 or 3 wherein the or each reactant solution is injected under pressure through a plurality of injection nozzles.

5. Process as claimed 2 or 3 wherein the or each reactant solution is injected under pressure through a plurality of divergently-arranged injection nozzles.

6. Process as claimed in claim 1 wherein the temperature of the reaction mixture is maintained within the range of from about 0° to about 5° C.

7. Process as claimed in claim 1 wherein the aluminium salt solution contains from about 0.4 to about 1.6 moles $Al^{3+}$ ion per liter.

8. Process as claimed in claim 7 wherein said solution contains from about 0.9 to about 1.4 moles $Al^{3+}$ ion per liter.

9. Process as claimed in claim 1 wherein said aluminium salt comprises aluminium chloride or aluminium sulphate.

10. Process as claimed in claim 9 wherein said salt is aluminium chloride.

11. Process as claimed in claim 1 wherein said alkaline solution is a mixed alkali metal carbonate and bicarbonate solution.

12. Process as claimed in claim 1 wherein said aqueous alkaline solution containing carbonate and bicarbonate anion contains sodium or potassium carbonate and sodium or potassium bicarbonate.

13. Process as claimed in claim 12, wherein said aqueous alkaline solution containing carbonate and bicarbonate anion comprises sodium carbonate and sodium bicarbonate.

14. Process as claimed in claim 1 wherein said aqueous alkaline solution containing carbonate and bicarbonate anion contains from about 0.1 to about 0.6 moles $CO_3^{2-}$ ion per liter and from about 0.2 to about 1.0 moles $HCO_3^-$ ion per liter.

15. Process as claimed in claim 14 wherein said aqueous alkaline solution containing carbonate and bicarbonate anions contains about 0.2 to about 0.3 moles $CO_3^{2-}$ ion per liter and about 0.5 to about 0.6 moles $HCO_3^-$ ion per liter.

16. Process as claimed in claim 1 wherein the reaction mixture in the initial reaction vessel is maintained at a pH from about 6.5 to about 6.8 and the reaction mixture in the subsequent reaction vessel is maintained at a pH which is lower (more acidic) relative to the pH of the initial reaction vessel, said pH of the initial reaction vessel being maintained by controlled additions of an aqueous acidic solution of an aluminum salt under vigorous agitation to maintain the reaction mixture in a substantially homogenous condition.

17. Process as claimed in claim 16 wherein said pH in the initial reaction vessel is about 6.5.

18. Process as claimed in claim 16 wherein said acidic solution contains about 0.2 to about 0.7 moles $Al^{3+}$ ion per liter.

19. Process as claimed in claim 18 wherein said solution contains about 0.4 to about 0.5 moles $Al^{3+}$ ion per liter.

20. Process as claimed in claim 16 wherein said aqueous acidic salt solution is a solution of aluminium chloride or aluminium sulphate.

21. Process as claimed in claim 20 wherein said salt is aluminium chloride.

22. Process as claimed in claim 1 or 16 wherein the initial reactor vessel is of relatively smaller capacity as compared with the subsequent reaction vessel, whereby the reaction mixture has a relatively shorter residence time in the initial reactor vessel and can be more efficiently subjected to homogenising agitation therein.

23. Process as claimed in claim 1 or 16 wherein after the gel-forming reaction is substantially complete, the gel precipitate is separated from excess liquids in a solid-sliquids separator device, and the solids residue is washed to reduce its content of soluble ions.

24. Process as claimed in claim 1 wherein after the gel-forming reaction is substantially complete, the gel is permitted to separate from the reaction mixture to form a gel precipitate phase and a supernatant phase containing small suspended particles of aluminium hydroxycarbonate gel, and including the steps of withdrawing the supernatant phase, and recycling supernatant phase to the initial reactor vessel.

25. Process as claimed in claim 24 including the step of recovering the gel precipitate phase, separating excess liquids therefrom in a solids-liquids separator device, and washing the solids residue to reduce its content of soluble ions.

26. Process as claimed in claim 24 wherein the solids residue is washed with water, and aqueous washings from the washing step are recycled to the initial reactor vessel.

27. Process as claimed in claim 24 wherein said aqueous alkaline solution is an alkali metal carbonate and bicarbonate solution, and including the step of washing the solids residue to provide a content of no more than about 0.5% by weight of alkali metal cation based on the weight of the wet gel product.

* * * * *